United States Patent
Wright et al.

(10) Patent No.: US 6,962,947 B2
(45) Date of Patent: *Nov. 8, 2005

(54) PRESSURE SWING CATALYST REGENERATION PROCEDURE FOR FISCHER-TROPSH CATALYST

(75) Inventors: Harold A. Wright, Ponca City, OK (US); Ajoy P. Raje, Stillwater, OK (US); Rafael L. Espinoza, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/035,093

(22) Filed: Jan. 13, 2005

(65) Prior Publication Data

US 2005/0124706 A1 Jun. 9, 2005

Related U.S. Application Data (60) Division of application No. 10/150,324, filed on May 16, 2002, now Pat. No. 6,869,978, and a continuation-in-part of application No. 09/713,051, filed on Nov. 15, 2000, now Pat. No. 6,486,220.
(60) Provisional application No. 60/291,924, filed on May 17, 2001, and provisional application No. 60/166,020, filed on Nov. 17, 1999.

(51) Int. Cl.[7] ............................ C07C 27/00; B01J 20/34
(52) U.S. Cl. ................. 518/709; 518/715; 518/716; 518/717; 518/720; 518/721; 502/20; 502/34
(58) Field of Search .................................. 518/709, 713, 518/715, 720, 721, 716, 717; 502/20, 34

(56) References Cited

U.S. PATENT DOCUMENTS

| | | | |
|---|---|---|---|
| 2,238,726 A | 4/1941 | Feisst et al. | |
| 2,415,861 A | 8/1947 | Brown et al. | |
| 2,453,035 A | 12/1948 | Wobker | |
| 2,500,519 A | 3/1950 | Clark | |

(Continued)

FOREIGN PATENT DOCUMENTS

| | | |
|---|---|---|
| CA | 2164462 | 6/1996 |
| CA | 94203562.7 | 12/1997 |
| EP | 0 220 343 | 5/1987 |
| EP | 0 363 537 | 4/1990 |
| GB | 2 222 531 | 3/1990 |
| GB | 2 258 826 | 2/1993 |
| WO | WO 97/17137 | 5/1997 |

OTHER PUBLICATIONS

PCT International Search Report for Application No. PCT/US00/31559, Dated Mar. 29, 2001; (5 p.).

PCT International Search Report for Application No. PCT/US02/15460 dated Aug. 21, 2002; (pp. 5).

*Primary Examiner*—J. Parsa
(74) *Attorney, Agent, or Firm*—Conley Rose P.C.

(57) ABSTRACT

A process is disclosed for regenerating a catalyst used in a process for synthesizing hydrocarbons. The synthesis process involves contacting a feed stream comprising hydrogen and carbon monoxide with a catalyst in a reaction zone maintained at conversion-promoting conditions effective to produce an effluent stream comprising hydrocarbons. The regeneration process involves contacting a deactivated Fischer-Tropsch catalyst with a regeneration gas under regeneration-promoting conditions that include a pressure lower than the mean Fischer-Tropsch reaction pressure, for a period of time sufficient to reactivate the Fischer-Tropsch catalyst.

22 Claims, 3 Drawing Sheets

U.S. PATENT DOCUMENTS

| | | | |
|---|---|---|---|
| 2,518,775 A | 8/1950 | Guyer | |
| 2,544,574 A | 3/1951 | Walker et al. | |
| 2,564,985 A | 8/1951 | Mayland | |
| 2,719,130 A | 9/1955 | Stewart | |
| 2,735,802 A | 2/1956 | Jahnig | |
| 3,958,957 A | 5/1976 | Koh et al. | |
| 4,151,190 A | 4/1979 | Murchison et al. | |
| 4,197,418 A | 4/1980 | Lee et al. | |
| 4,405,343 A | 9/1983 | Othmer | |
| 4,585,798 A | 4/1986 | Beuther et al. | |
| 4,595,703 A | 6/1986 | Payne et al. | |
| 4,600,499 A | 7/1986 | Hettinger, Jr. | |
| 4,606,811 A | 8/1986 | Hettinger | |
| 4,733,528 A | 3/1988 | Pinto | |
| 4,738,948 A | 4/1988 | Iglesia et al. | |
| 4,744,883 A | 5/1988 | Hettinge, Jr. | |
| 4,822,824 A | 4/1989 | Iglesia et al. | |
| 4,978,689 A | 12/1990 | Bell et al. | |
| 5,260,239 A | 11/1993 | Hsia | |
| 5,268,344 A | 12/1993 | Pedrick et al. | |
| 5,283,216 A | 2/1994 | Mitchell | |
| 5,356,845 A | 10/1994 | Clavenna et al. | |
| 5,397,806 A | 3/1995 | Soled et al. | |
| 5,545,674 A | 8/1996 | Behrmann et al. | |
| 5,585,316 A | 12/1996 | Nay et al. | |
| 5,728,918 A | 3/1998 | Nay et al. | |
| 5,811,468 A | 9/1998 | Chang et al. | |
| 5,817,701 A | 10/1998 | Leviness et al. | |
| 5,817,702 A | 10/1998 | Behrmann et al. | |
| 5,821,270 A | 10/1998 | Chang et al. | |
| 5,844,005 A | 12/1998 | Bauman et al. | |
| 5,929,126 A | 7/1999 | Koveal et al. | |
| 5,958,986 A | 9/1999 | Mart et al. | |
| 6,486,220 B1 * | 11/2002 | Wright | 518/709 |
| 6,869,978 B2 * | 3/2005 | Wright et al. | 518/709 |

* cited by examiner

PRESSURE SWING CATALYST REGENERATION PROCEDURE FOR FISCHER-TROPSH CATALYST

CROSS-REFERENCE TO RELATED APPLICATIONS

This application is a divisional application of U.S. patent application Ser. No. 10/150,324 filed May 16, 2002, now U.S. Pat. No. 6,869,978 entitled "Pressure Swing Catalyst Regeneration Procedure for Fischer-Tropsch Catalyst" which claims the benefit of priority from U.S. provisional application Ser. No. 60/291,924, filed May 17, 2001, entitled Pressure Swing Catalyst Regeneration Procedure for Fischer-Tropsch Catalyst. Further, the present application is a continuation-in-part application of U.S. utility application Ser. No. 09/713,051, filed Nov. 15, 2000, now U.S. Pat. No. 6,486,220, and entitled Regeneration Procedure for Fischer-Tropsch Catalyst, which claims the benefit of provisional application Ser. No. 60/166,020, filed Nov. 17, 1999, and entitled Regeneration Procedure for Fischer-Tropsch Catalyst. Each of the above-listed applications is hereby incorporated herein by reference for all purposes.

STATEMENT REGARDING FEDERALLY SPONSORED RESEARCH OR DEVELOPMENT

Not applicable.

FIELD OF THE INVENTION

The present invention relates to a process for the preparation of hydrocarbons from synthesis gas, (i.e., a mixture of carbon monoxide and hydrogen), typically labeled the Fischer-Tropsch process. More particularly, the present invention relates to a regeneration method for a Fischer-Tropsch catalyst. Still more particularly, the present invention relates to the use of a regeneration pressure lower than the Fischer-Tropsch reaction pressure to remove hydrocarbon deposits and regenerate a deactivated Fischer-Tropsch catalyst.

BACKGROUND OF THE INVENTION

Large quantities of methane, the main component of natural gas, are available in many areas of the world. However, most natural gas is situated in areas that are geographically remote from population and industrial centers. The costs of compression, transportation, and storage make the use of this remote gas economically unattractive. To improve the economics of natural gas use, much research has focused on the use of methane as a starting material for the production of higher hydrocarbons and hydrocarbon liquids.

As a result, various technologies for the conversion of methane to hydrocarbons have evolved. The conversion is typically carried out in two steps. In the first step methane is reformed with water or partially oxidized with oxygen to produce carbon monoxide and hydrogen (i.e., synthesis gas or syngas). In a second step, the syngas is converted to hydrocarbons.

This second step, the preparation of hydrocarbons from synthesis gas is well known in the art and is usually referred to as Fischer-Tropsch synthesis, the Fischer-Tropsch process, or Fischer-Tropsch reaction(s). The Fischer-Tropsch reaction involves the catalytic hydrogenation of carbon monoxide to produce a variety of products ranging from methane to heavy hydrocarbons (up to $C_{80}$ and higher) as well as a variety of oxygenated hydrocarbons. The methanation reaction was first described in the early 1900's, and the later work by Fischer and Tropsch dealing with higher hydrocarbon synthesis was described in the 1920's.

Catalysts for use in such synthesis usually contain a catalytically active metal of Groups 8, 9, 10 (in the New notation of the periodic table of the elements, which is followed throughout). In particular, iron, cobalt, nickel, and ruthenium have been used as the catalytically active metals. Cobalt, iron and ruthenium have been found to be most suitable for catalyzing a process in which synthesis gas is converted to primarily hydrocarbons having five or more carbon atoms (i.e., where the $C_{5+}$ selectivity of the catalyst is high). Additionally, the catalysts often contain one or more promoters and a support or carrier material. Ruthenium is a widely used promoter for cobalt catalysts.

The Fischer-Tropsch synthesis reactions are highly exothermic and reaction vessels must be designed for adequate heat exchange capacity. Because the feed streams to Fischer-Tropsch reaction vessels are gases, while the product streams include liquids, the reaction vessels must have the ability to continuously produce and remove the desired range of liquid hydrocarbon products. The first major commercial use of the Fischer-Tropsch process was in Germany during the 1930's. More than 10,000 B/D (barrels per day) of products were manufactured with a cobalt based catalyst in a fixed-bed reactor. This work was described by Fischer and Pichler in German Patent 731,295 issued Aug. 2, 1936.

Motivated by the hope of producing high-grade gasoline from natural gas, research on the possible use of the fluidized bed for Fischer-Tropsch synthesis was conducted in the United States in the mid-1940s. Based on laboratory results, Hydrocarbon Research, Inc. constructed a dense-phase fluidized bed reactor, the Hydrocol unit, at Carthage, Tex., using powdered iron as the catalyst. Due to disappointing levels of conversion, scale-up problems, and rising natural gas prices, operations at this plant were suspended in 1957. Research continued, however, on developing Fischer-Tropsch reactors, such as slurry-bubble columns, as disclosed in U.S. Pat. No. 5,348,982. Despite significant advances, certain areas of the Fischer-Tropsch technology still have room for improvement. One potential technology in need of improvement relates to regeneration of the Fischer-Tropsch catalyst.

After a period of time in operation, a catalyst will become deactivated, losing its effectiveness for synthesis gas conversion to a degree that makes it uneconomical at best and inoperative at worst. At this point, the catalyst can be either replaced or regenerated. Because the catalysts tend to be relatively expensive, regeneration is preferred over replacement. Catalyst systems can become deactivated by a number of processes, including coking, sintering, oxidation, and poisoning. The process chiefly responsible for deactivation varies among catalyst systems. Therefore, the preferred method for regeneration tends to depend on the catalyst system to be regenerated.

Research is continuing on the development of more efficient Fischer-Tropsch catalyst systems and catalyst systems that can be more effectively regenerated. In particular, a number of studies describe the use of various gases, including hydrogen, air, and carbon monoxide to regenerate a variety transition metal containing Fischer-Tropsch catalyst systems.

U.S. Pat. No. 3,958,957, issued on May 25, 1976, describes a carbon-alkali metal catalyst, used for conversion of synthesis gas to methane and higher hydrocarbons at a pressure of 100–1500 psig and a temperature of 300–550° F.

at a typical gas hourly space velocity of 1000 volumes gas/hr/volume catalyst. The carbon-alkali metal catalyst can be regenerated with air oxidation.

U.S. Pat. No. 4,151,190, issued on Apr. 24, 1979, describes a catalyst comprising at least one of a sulfide, oxide, or metal of Mo, W, Re, Ru, Ni, or Pt, at least one of a hydroxide, oxide, or salt of Li, Na K, Rb, Cs, Mg, Ca, Sr, Ba, or Th, and a support, used for conversion of synthesis gas with an $H_2$:CO ratio of 0.25-4.0, preferably 0.5–1.5, to $C_2$–$C_4$ hydrocarbons at a pressure of 15–2000 psia and a temperature of 250–500° C. at a typical gas hourly space velocity of 300 v/hr/v. This catalyst can be regenerated by contacting it with hydrogen gas at 500–600° C. for 16 hours.

U.S. Pat. No. 4,738,948, issued on Apr. 19, 1988, describes a catalyst comprising cobalt and ruthenium at an atomic ratio of 10-400, on a refractory carrier, such as titania or silica. The catalyst is used for conversion of synthesis gas with an $H_2$:CO ratio of 0.5-10, preferably 0.5–4, to $C_5$–$C_{40}$ hydrocarbons at a pressure of 80–600 psig and at a temperature of 160–300° C., at a gas hourly space velocity of 100–5000 v/hr/v. This catalyst can be regenerated by contacting it with hydrogen gas at 150–300° C., preferably 190–260° C., for 8–10 hours.

U.S. Pat. No. 5,728,918, issued on Mar. 17, 1998, describes a catalyst comprising cobalt on a support, used for conversion of synthesis gas with an $H_2$:CO ratio of 1-3, preferably 1.8–2.2, to $C_{5+}$ hydrocarbons at a pressure of 1–100 bar and at a temperature of 150–300° C., at a typical gas hourly space velocity of 1000–6000 v/hr/v. This catalyst can be regenerated by contacting it with a gas containing carbon monoxide and less than 30% hydrogen, at a temperature more than 10° C. above Fischer-Tropsch conditions and in the range 100–500° C., and at a pressure of 0.5–10 bar, for at least 10 minutes, preferably 1–12 hours. The contact time period depends on temperature and gas hourly space velocity. The U.S. Pat. No. 5,728,918 also teaches an activation procedure, which may include a first step of contacting the catalyst with a gas containing molecular oxygen, preferably air, at 200–600° C., at atmospheric pressure, for more than 30 minutes, and preferably for 1–48 hours.

U.S. Pat. No. 4,595,703, issued on Jun. 17, 1986, describes a catalyst comprising cobalt or thoria promoted cobalt on a titania support, used for conversion of synthesis gas with an $H_2$:CO ratio of 0.5-4, preferably 2–3, to $C_{10+}$ hydrocarbons at a pressure of preferably 80–600 psig, and at a temperature of 160–290° C., at a gas hourly space velocity of 100–5000 v/hr/v. This catalyst can be regenerated by contacting it with hydrogen gas, or a gas which is inert or non-reactive at stripping conditions such as nitrogen, carbon monoxide, or methane, at a temperature substantially the same as Fischer-Tropsch conditions. If it is necessary to remove coke deposits from the catalyst, the catalyst can be contacted with a dilute oxygen-containing gas, at oxygen partial pressure of at least 0.1 psig, at 300–550° C., for a time sufficient to remove coke deposits, followed by contact with a reducing gas containing hydrogen, at a temperature of 200–575° C. and at a pressure of 1–40 atmospheres, for 0.5–24 hours.

U.S. Pat. No. 4,585,798 issued on Apr. 29, 1986, describes a catalyst comprising cobalt and ruthenium in an atomic ratio greater than about 200:1 and, preferably, a promoter, such as a Group IIIB or IVB metal oxide, on an alumina support, used for conversion of synthesis gas to hydrocarbons at a pressure of preferably 1–100 atmospheres and at a temperature of 160–350° C., at a gas hourly space velocity less than 20,000 v/hr/v, preferably 100–5000 v/hr/v, especially 1000–2500 v/hr/v, which is activated prior to use by reduction with hydrogen gas, followed by oxidation with diluted air, followed by further reduction with hydrogen gas.

Despite the vast amount of research effort in this field, currently known methods of regeneration of Fischer-Tropsch catalysts are not always sufficiently effective for a particular catalyst system. Among the main deactivation mechanisms for cobalt based catalysts are sulfur poisoning [e.g. R. L. Espinoza, et al, Applied Catalysis A:General 186 (1999)13], metal oxidation [e.g. D. Schanke et al, Catal. Lett. 34 (1995) 269] and surface condensation of heavy hydrocarbons [e.g. E. Iglesia et el, J. Catal. 143 (1993) 345]. The removal of heavy hydrocarbons, deposited in the pores of a used catalyst, is therefore one of the challenges to efficient commercialization of slurry bed technology for the Fischer-Tropsch reaction.

In a slurry bed reactor, the Fischer-Tropsch catalyst particles are suspended in liquid reaction products (heavy hydrocarbons), predominantly wax. These heavy hydrocarbons may include heavy hydrocarbons formed in the Fischer-Tropsch reaction. In a fixed bed reactor, the catalyst particles, though not suspended in heavy hydrocarbons, will contain and/or become coated with heavy hydrocarbons as reaction proceeds. One of the deactivation mechanisms of the catalyst is the deposition of very heavy hydrocarbons into the catalyst pores and/or on the surface of the catalyst particles. Hydrogen gas, conventionally maintained at reaction pressure, has been used to remove a portion of this material through hydrogenation of the heavy hydrocarbon. However, this method has the disadvantages that hydrogenation may be incomplete and that the hydrogenated hydrocarbon may remain deposited in the pores of the catalyst and/or on the surface of the catalyst particles. Also, a certain degree of hydrogenolysis, that is, destruction of valuable heavy hydrocarbons may occur, producing gaseous hydrocarbons of lower commercial value.

Hence, there is still a great need to identify new regeneration methods which can be used concurrently and/or periodically with contacting regenerated catalyst with synthesis gas, so as to maximize the regenerated catalyst activity and thus enhance the process economics.

SUMMARY OF THE INVENTION

This invention relates to a process and catalyst for producing hydrocarbons, and includes a method for catalyst regeneration. The Fischer-Tropsch synthesis process includes contacting a feed stream comprising hydrogen and carbon monoxide with a catalyst in a reaction zone maintained at conversion-promoting conditions effective to produce an effluent stream comprising hydrocarbons.

The regeneration process comprises contacting a deactivated Fischer-Tropsch catalyst with a regeneration gas under regeneration-promoting conditions, for a period of time sufficient to reactivate the Fischer-Tropsch catalyst. The pressure is preferably substantially less than the mean Fischer-Tropsch reaction pressure. More specifically, the regeneration-promoting conditions in accordance with the present invention include a temperature between about 250° C. and 350° C. and a pressure between about 0 psig (0.1 MPa) and about 350 psig (2.5 MPa). Contact with the regeneration gas is maintained for a period of time sufficient to reactivate the Fischer-Tropsch catalyst. The regeneration gas is preferably selected from the group consisting of hydrogen-containing gases, oxygen-containing gases, steam, inert gases such as nitrogen, and non-explosive combinations thereof. The volume ratio of the regeneration gas to the deactivated Fischer-Tropsch catalyst is preferably at least about 1 Standard Liter per hour per gram of catalyst. It will be understood that in some instances the regeneration gas may be generated by passing a liquid through a heating zone before contact with the catalyst; and it will be further understood that references herein to regeneration gas include streams that may contain some liquid.

This invention further includes a process of cycling between the synthesis process and the regeneration process.

BRIEF DESCRIPTION OF THE DRAWINGS

For a detailed description of the preferred embodiment of the present invention, reference will now be made to the accompanying drawings, wherein.

DETAILED DESCRIPTION OF A PREFERRED EMBODIMENT

Synthesis Reaction

The feed gases charged to the synthesis process that precedes the present regeneration process comprise hydrogen, or a hydrogen source, and carbon monoxide. $H_2$/CO mixtures suitable as a feedstock for conversion to hydrocarbons according to the synthesis process can be obtained from light hydrocarbons such as methane by means of steam reforming, partial oxidation, or other processes known in the art. It is preferred that the molar ratio of hydrogen to carbon monoxide in the feed be greater than 0.5:1 (e.g., from about 0.67:1 to 2.5:1). The feed gas stream may contain hydrogen and carbon monoxide in a molar ratio of about 2:1. The feed gas stream may also contain carbon dioxide. The feed gas stream should contain a low concentration of compounds or elements that have a deleterious effect on the catalyst, such as poisons. For example, the feed gas may need to be pre-treated to ensure that it contains low concentrations of sulfur or nitrogen compounds such as hydrogen sulfide, ammonia and carbonyl sulfides.

The feed gas is contacted with the catalyst in a reaction zone. Mechanical arrangements of conventional design may be employed as the reaction zone including, for example, fixed bed, fluidized bed, slurry phase, slurry bubble column, reactive distillation column, or ebulliating bed reactors, among others, may be used. The size and physical form of the catalyst may vary, depending on the reactor in which it is to be used.

Catalyst Support

The active catalyst components are preferably carried or supported on a suitable support. Suitable supports include titania, titania/alumina, zirconia, alumina, silica, silica/alumina, and the like. Further, suitable supports include those disclosed in commonly assigned U.S. Pat. No. 6,368,997, issued from U.S. application Ser. No. 09/314,921, entitled "Fischer-Tropsch Catalysts and Processes Using Fluorided Supports; U.S. Pat. No. 6,365,544, issued from U.S. application Ser. No. 09/314,920, entitled "Fischer-Tropsch Processes and Catalysts Using Fluorided Alumina Supports", and co-pending U.S. application Ser. No. 09/898,287, entitled "Fischer-Tropsch Processes and Catalysts Using Aluminum Borate Supports", each hereby incorporated herein by reference. Thus, suitable supports further may include fluorided metal oxides, fluorided alumina, aluminum fluoride, borated alumina, and aluminum borate.

Metals can be supported on aluminum fluoride or on fluorided alumina in a variety of ways. For example, U.S. Pat. No. 4,766,260 discloses the preparation of metals such as cobalt on a fluorided alumina support using impregnation techniques to support the metal. U.S. Pat. No. 5,559,069 discloses the preparation of a multiphase catalyst composition comprising various metal fluorides including cobalt fluoride homogeneously dispersed with aluminum fluoride. PCT Int. Publ. No. 97/19751 discloses the preparation of multiphase catalyst compositions comprising metallic ruthenium homogeneously dispersed with various metal fluorides including aluminum fluoride.

Phases of aluminum fluoride such as eta, beta, theta and kappa can be prepared as described in U.S. Pat. No. 5,393,509, U.S. Pat. No. 5,417,954, and U.S. Pat. No. 5,460,795.

Aluminas that have been treated with fluosilicic acid ($H_2SiF_6$) such as those described in European Patent Application EP 497,436 can also be used as a support. The support disclosed therein comprises from about 0.5 to about 10 weight percent of fluorine, from 0.5 to about 5 weight percent of silica and from about 85 to about 99 weight percent of alumina.

Catalyst

Catalysts which are contemplated to be regenerated by the present method include any of the Fischer-Tropsch catalysts known in the art, such as cobalt, ruthenium, cobalt/ruthenium, cobalt/rhenium, other cobalt/promoter systems, iron, and nickel. In particular, the catalyst may include cobalt and ruthenium. The amount of cobalt and ruthenium present in the catalyst may vary widely. Typically, the catalyst comprises cobalt and ruthenium in an amount from about 1 to 50% by weight (as the metal) of the total weight of catalytic metal and support, preferably from about 1 to 30% by weight, and more preferably from about 1 to 25% by weight. Ruthenium is added to the support in a concentration sufficient to provide a weight ratio of elemental ruthenium to elemental cobalt of from about 0.001:1 to about 0.25:1, and preferably from about 0.001:1 to about 0.05:1 (dry basis).

The catalyst may also contain other promoters. When the catalytic metal is iron, cobalt, nickel, and/or ruthenium, suitable promoters include at least one promoter selected from the group consisting of Group 1 metals (i.e., Na, K, Rb, Cs), Sr, Group 11 metals (i.e., Cu, Ag, and Au) Sc, Group 4 metals (i.e., Ti, Zr and Hf), Group 5 metals (i.e., V, Nb and Ta), and Rh, Pd, Os, Ir, Pt and Re. Preferably, any additional promoters for the cobalt and/or ruthenium catalysts are selected from Sc, Ti, Zr, Hf, Rh, Pd, Os, Ir, Pt, Re, Nb, Cu, Ag and Ta. Preferably, any additional promoters for the iron catalysts are selected from Na, K, Rb, Cs and Sr. The amount of additional promoter, if present, is typically between 0.001 and 40 parts by weight per 100 parts of carrier. Further, the amount of promoter is preferably added to a cobalt-containing catalyst in a concentration sufficient to provide a weight ratio of elemental promoter to elemental cobalt of from about 0.00005:1 to about 0.5:1, and preferably from about 0.0005:1 to about 0.01:1 (dry basis).

It will be understood that the promoter is not limited to those listed above and may be any known Fischer-Tropsch promoter, including those disclosed in any of the above-referenced patents and publications. The promoter is preferably one that improves the activity of a catalyst in the Fischer-Tropsch reaction. Further, suitable promoters, and concentrations thereof, include those disclosed in commonly assigned co-pending U.S. Pat. No. 6,333,294 issued from U.S. applications Ser. No. 09/314,811, entitled "Fischer-Tropsch Processes and Catalysts Using Promoters", and U.S. utility application Ser. No. 09/804,271, entitled "Fischer-Tropsch Processes and Catalysts with Promoters", and U.S. utility application Ser. No. 10/047,231, entitled "Boron Promoted Catalysts and Fischer-Tropsch Processes", each hereby incorporated herein by reference. Thus suitable promoters include boron, vanadium, phosphorous, manganese, and alkali metals.

Catalysts which may be regenerated by the present method may be prepared by any of the methods known to those skilled in the art. By way of illustration and not limitation, such methods include impregnating the catalytically active compounds or precursors onto a support, extruding one or more catalytically active compounds or precursors together with support material to prepare catalyst extrudates, and/or precipitating the catalytically active compounds or precursors onto a support. Accordingly, the supported catalysts of the present invention may be used in the form of powders, particles, pellets, monoliths, honeycombs, packed beds, foams, and aerogels.

The most preferred method of preparation may vary, as will be recognized by those skilled in the art, depending for example on the desired catalyst particle size. Those skilled in the art will be able to select the most suitable method for a given set of requirements.

One method of preparing a supported metal catalyst (e.g., a supported cobalt, cobalt/ruthenium, or cobalt/ruthenium/promoter catalyst) is by incipient wetness impregnation of the support with an aqueous solution of a soluble metal salt such as nitrate, acetate, acetylacetonate or the like. Another method of preparing a supported metal catalyst is by a melt impregnation technique, which involves preparing the supported metal catalyst from a molten metal salt. One preferred method is to impregnate the support with a molten metal nitrate (e.g., $Co(NO_3)_2 \cdot 6H_2O$). Alternatively, the support can be impregnated with a solution of a zero valent metal precursor. One preferred method is to impregnate the support with a solution of zero valent cobalt such as $Co_2(CO)_8$, $Co_4(CO)_2$ or the like in a suitable organic solvent (e.g., toluene). Suitable ruthenium compounds are the common water soluble ones, e.g., ruthenium heptoxide ($Ru_2O_7$) and ammonium perruthenate ($NH_4RuO_4$).

The impregnated support is dried and reduced with hydrogen or a hydrogen containing gas. The hydrogen reduction step may not be necessary if the catalyst is prepared with zero valent cobalt. In another preferred method, the impregnated support is dried, oxidized with air or oxygen and reduced in the presence of hydrogen.

Typically, at least a portion of the metal(s) of the catalytic metal component (a) of the catalysts of the present invention is present in a reduced state (i.e., in the metallic state). Therefore, it is normally advantageous to activate the catalyst prior to use by a reduction treatment, in the presence of hydrogen at an elevated temperature. Typically, the catalyst is treated with hydrogen at a temperature in the range of from about 75° C. to about 500° C., for about 0.5 to about 24 hours at a pressure of about 1 to about 75 atm. Pure hydrogen may be used in the reduction treatment, as may a mixture of hydrogen and an inert gas such as nitrogen, or a mixture of hydrogen and other gases as are known in the art, such as carbon monoxide and carbon dioxide. Reduction with pure hydrogen and reduction with a mixture of hydrogen and carbon monoxide are preferred. The amount of hydrogen may range from about 1% to about 100% by volume.

Catalysis

The Fischer-Tropsch process is typically run in a continuous mode. In this mode, the gas hourly space velocity through the reaction zone may range from about 100 volumes/hour/volume catalyst (v/hr/v) to about 15,000 v/hr/v, preferably from about 2000 v/hr/v to about 10,000 v/hr/v. The reaction zone temperature is typically in the range from about 160° C. to about 300° C. Preferably, the reaction zone is operated at conversion promoting conditions at temperatures from about 190° C. to about 260° C. The reaction zone pressure is typically in the range of about 80 psig (653 kPa) to about 1000 psig (6994 kPa), preferably from 80 psig (653 kPa) to about 600 psig (4237 kPa), more preferably from about 140 psig (1066 kPa) to about 450 psig (2858 kPa), more preferably from about 300 psig to about 450 psig.

The products resulting from Fischer-Tropsch synthesis will have a range of molecular weights. Typically, the carbon number range of the product hydrocarbons will start at methane and continue to the limits observable by modern analysis, about 50 to 100 carbons per molecule. The catalyst of the present process is particularly useful for making hydrocarbons having five or more carbon atoms, especially when the above-referenced preferred space velocity, temperature and pressure ranges are employed.

Regeneration

Catalysts, such as those described above, tend to become deactivated. The present method of regenerating a catalyst preferably includes passing the catalyst from a reaction zone maintained at a reaction pressure to a regeneration zone maintained at a regeneration pressure less than the reaction pressure. The regeneration pressure is preferably between about 10 psig and about 350 psig, more preferably between about 50 psig and about 350 psig. A portion of the heavy hydrocarbons is preferably removed from the catalyst surface via vaporization. The regeneration pressure is preferably set at a predetermined value selected to effect volatilization of a portion of the heavy hydrocarbon that would otherwise be present as liquids at normal operating pressure. In combination, or alternatively, the regeneration pressure is preferably set at a predetermined value selected to effect volatilization of heavier than $C_{40}$.

It will be understood that reaction pressure, as used herein, may be the mean reaction pressure. Further, it will be understood that regeneration pressure, as used herein, may be the mean regeneration pressure. The mean may be a time average taken at a fixed location in the reactor. Alternatively or in combination, the mean may be a spatial average taken at a fixed time.

Further, it will be appreciated that heavy hydrocarbons may include different molecular weight hydrocarbons according to the system. Heavy hydrocarbons, as used herein preferably include those hydrocarbons with a molecular weight of at least 500. Alternatively, or in combination, very heavy hydrocarbons, as used herein, preferably include those hydrocarbons including 40 or more carbon atoms.

Regeneration preferably includes contacting the catalyst with a regeneration gas in a regeneration zone. The regeneration gas may be any conventional regeneration gas, preferably a regeneration gas for a Fischer-Tropsch catalyst. Thus, the regeneration gas is preferably chosen from among hydrogen-containing gases, such as hydrogen gas, oxygen-containing gases, such as air and oxygen gas, steam, inert gases such as nitrogen and the like, and non-explosive combinations thereof. For example, one preferred regeneration gas includes steam and hydrogen. The hydrogen is preferably present with the steam in an amount not exceeding 5% by volume of the total regeneration gas.

Fischer-Tropsch synthesis conditions may be maintained, but preferably the pressure is reduced and the temperature is raised during regeneration. The temperature is preferably increased by an amount between 0° C. and 150° C. from the operating temperature of the Fischer-Tropsch synthesis. Regeneration temperatures can thus range from about 200° C. to about 450° C., more preferably from about 220° C. to about 450° C., preferably from about 250° C. to about 350° C. Likewise, the pressure is preferably reduced by between 10 psig and about 300 psig from the pressure of the Fischer-Tropsch synthesis. Pressures can thus range from about 0 psig to about 350 psig. Contact between the regeneration gas and the catalyst is maintained for at least 5 minutes and preferably for at least 4 hours. At least 0.25 Standard L/hr, preferably at least 0.5 Standard L/hr, and most preferably at least 1 Standard L/hr/ of regeneration gas are used for each gram of catalyst.

Under these regeneration conditions, it has been found that the activity of certain catalysts will return to levels at or exceeding 50% of the pre-deactivation activity.

Regeneration Using Steam

In a regeneration process in which the regeneration gas includes steam, there is an optimal temperature range. It has been discovered that at lower temperatures, the steam does not regenerate the catalyst. At high temperatures, the steam causes detrimental selectivity changes to the catalyst. Steam is an oxidizing agent that can oxidize cobalt metal sites on the catalyst to cobalt oxide, which is not catalytic for Fischer-Tropsch synthesis. There is significant literature stating that water or steam has a significant deactivating effect on the Fischer-Tropsch reaction. Hence, it was expected that steam would deactivate the catalyst further. Contrary to these expectations, it has been discovered that there exists a temperature range in which contact with steam can cause an increase in catalytic activity. Depending on the catalyst and the degree of deactivation, it has been found that activity can be increased to at least 50% of the pre-deactivation activity and sometimes as much as 100% of the pre-deactivation activity.

While not wishing to be bound by any theory, it is believed that steam may oxidize coke on the catalyst surface and/or remove the heavy hydrocarbons on the catalyst surface. If the primary deactivation mechanism is coking and/or deposition of heavy hydrocarbons, then steam will work at least as well as hydrogen gas. Hydrogen gas may work better in cases where oxidation is one of the mechanisms of deactivation.

It is believed that there are at least two general classes of catalyst where coking may be the key deactivation mechanism. The first class of catalyst is cobalt-containing supported catalysts where the support has high acidity. Acid site coking is well known in the art as a mechanism of the coking reaction. As an example, fluorided supports are highly acidic. The second class of catalyst is cobalt-containing catalysts having a high initial activity. A high initial activity occurs when the initial CO conversion is greater than about 60%. With high activity, localized surface temperatures on a catalyst particle can be very high, aiding in the coking mechanism.

Reaction/Regeneration Cycle

According to an embodiment of the present invention, a process for cycling between reaction and regeneration includes applying a pressure swing condition to a catalyst. Pressure swing, as termed herein, designates a cycle in pressure from a reaction pressure to a lower regeneration pressure and back to the reaction pressure.

Figure 1:
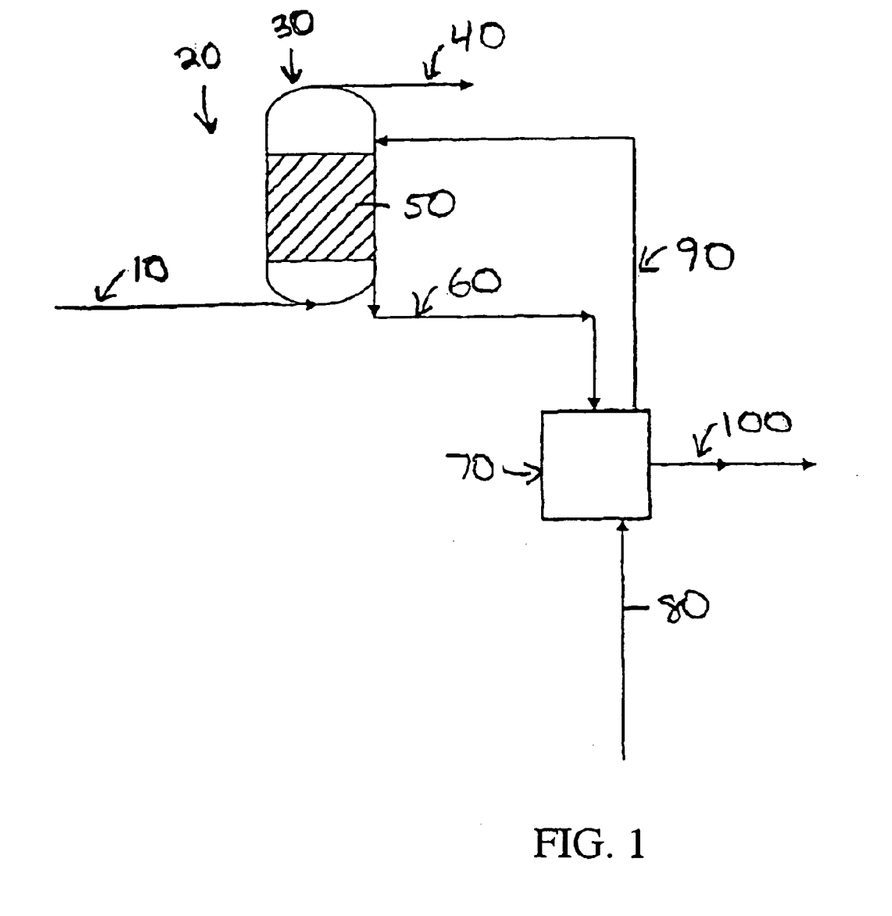
FIG. 1 is a schematic diagram of a coupled reaction/regeneration process, particularly suited to slurry bed reactors, according to an embodiment of the present invention.

Referring to FIG. 1, a cyclical process preferably includes passing a feed stream 10 to a reaction zone 20. Feed stream 10 preferably includes synthesis gas. Reaction zone 20 preferably includes a reactor 30. Reactor 30 is preferably a slurry bed reactor. Slurry bed reactors are known and are described for example in U.S. Pat. No. 5,348,982, hereby incorporated herein by reference.

A light product 40 preferably exits from reactor 30 during operation, preferably from near the top of the reactor. Light product 40 may include water, a byproduct of Fischer-Tropsch synthesis, and un-reacted synthesis gas components, that is carbon monoxide and hydrogen. Light product 40 may further include any reaction products that are typically gaseous under Fischer-Tropsch reaction conditions.

Reactor 30 preferably contains a catalyst slurry 50. Slurry 50 includes solid catalyst, preferably particulate catalyst, in a liquid suspension. Used slurry 60 preferably exits reactor 30 during operation. Used slurry 60 includes catalyst particles, some of which may be deactivated by heavy hydrocarbons.

Used slurry 60, containing used catalyst, preferably passes to regenerator 70. Regenerator 70 is preferably a variable-pressure regeneration unit. A rejuvenation gas 80 preferably passes into regenerator 70. A described in more detail above in the section entitled "Regeneration", the rejuvenation gas, also termed regeneration gas, is preferably any Fischer-Tropsch regeneration gas, including, but not limited to, a hydrogen-containing gas, and steam. The pressure of the regenerator is preferably maintained so as to volatilize heavy hydrocarbons. Further, as described in more detail above, in the section entitled "Regeneration", when the regeneration gas is hydrogen, the hydrogen may hydrogenate one or more heavy hydrocarbons deposited on the catalyst.

Regenerator 70 is operated in semi-batch mode. After the used slurry 60 enters the regenerator, the rejuvenation gas is started and the pressure of the vessel is reduced to pressure sufficient to volatilize heavy hydrocarbons. After a sufficient treatment, the pressure in the regenerator 70 can be raised and the rejuvenated catalyst (90) passes back to the reactor 30 preferably still in a slurry.

Alternatively, or in combination reactor slurry 100 is passed from regenerator 70 to a filtration unit (not shown.)

Figure 2:
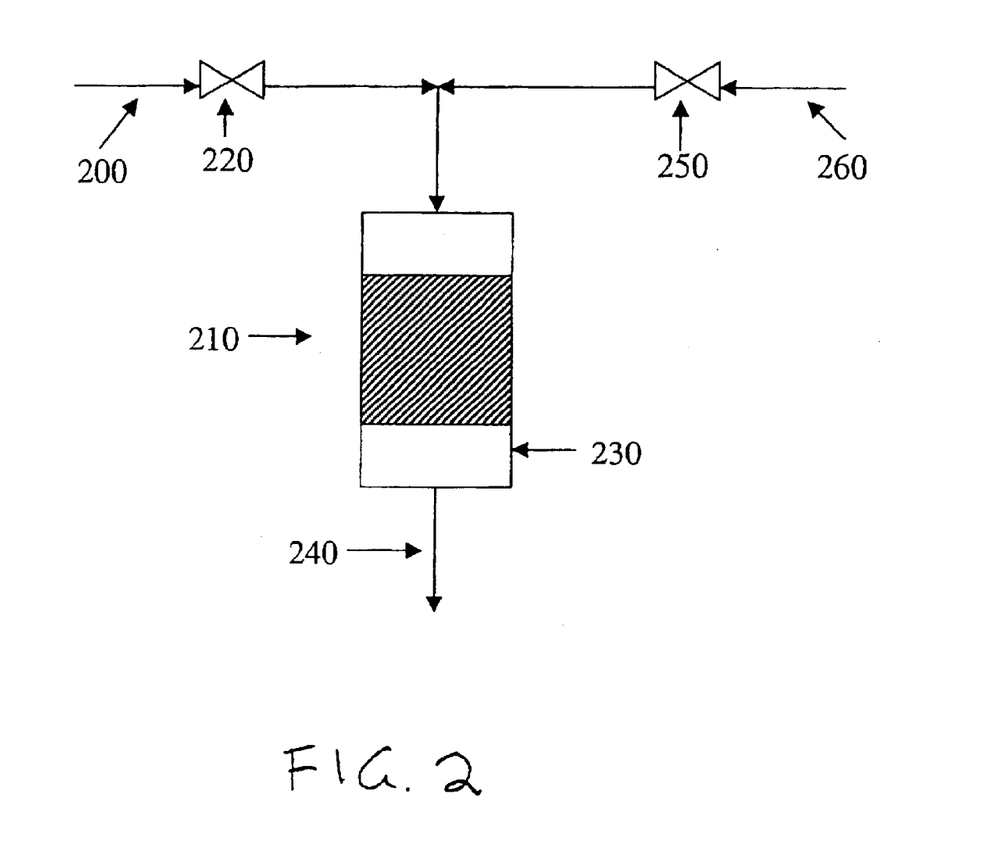
FIG. 2 is a schematic diagram of a second coupled reaction/regeneration process, particularly suited to fixed bed reactors, according to an embodiment of the present invention.

Referring now to FIG. 2 an alternative embodiment of the present invention more suitable to reactors other than slurry reactors is shown. However, this embodiment could be used with any reactor type. A feed stream 200, preferably including synthesis gas, feeds a reaction zone 210 through a valve 220. Reaction zone 210 contains a reactor 230. A product stream 240 from the reactor may include water, a byproduct of Fischer-Tropsch synthesis, un-reacted synthesis gas components, that is carbon monoxide and hydrogen and hydrocarbon products produced under Fischer-Tropsch reaction conditions.

Reactor 230 contains a solid catalyst. The catalyst deactivates over a period of time. When the activity of the catalyst falls to a pre-determined level, valve 220 is closed separating feed stream 200 from reactor 230. Simultaneously, valve 250 is opened letting a regeneration gas stream 260 into reactor 230. Reactor 230 may be de-pressurized and heated (if desirable) to the desired regeneration conditions. As described in more detail above in the section entitled "Regeneration", the rejuvenation gas, also termed regeneration gas, is preferably any Fischer-Tropsch regeneration gas, including, but not limited to, a hydrogen-containing gas, and steam. The pressure during regeneration is preferably maintained so as to volatilize heavy hydrocarbons.

After a suitable length of time, reactor 230 is cooled (if desirable) to reaction temperature and valve 250 is closed separating regeneration gas stream 260 from reactor 230. Simultaneously, valve 220 is opened letting in feed stream 200 to reactor 230. Reactor 230 is subsequently pressurized to the desired reaction pressure. By this process, reactor 230 is cycled between conditions which promote the Fischer-Tropsch reaction and conditions which promote catalyst regeneration.

It will be appreciated that while the Fischer-Tropsch reaction has been described with respect to the production of hydrocarbons, the Fischer-Tropsch reaction, or Fischer-Tropsch process, may include any catalytic transformation of synthesis gas to form any organic reaction product, that is containing at least one specie of organic molecule. Organic molecules include molecules that contain carbon and hydrogen, such as hydrocarbons, oxygenates, and the like. Hydrocarbons include molecules limited to carbon and hydrogen, such as paraffins (alkanes), straight-chain paraffins, olefins (alkenes), and the like. Oxygenates include molecules that include carbon, hydrogen, and oxygen, such as alcohols, and the like.

Further, it will be understood that while reaction has been described with respect to the Fischer-Tropsch catalysis, the present process may be applied to any reaction or reaction system that involves the contact of a catalyst with heavy hydrocarbons. Exemplary reactions and systems for which the present process is contemplated include methanol synthesis, hydrogenation reactions, and petroleum residue hydroprocessing.

Without further elaboration, it is believed that one skilled in the art can, using the description herein, utilize the present invention to its fullest extent. The following embodiments are to be construed as illustrative, and not as constraining the scope of the present invention in any way whatsoever.

EXAMPLE 1

A fixed bed reactor was used for the first example. The fixed bed was a 1 in. tubular reactor packed with 6 grams of catalyst and about 30 grams of diluent (glass beads). A thermocouple in the middle of the bed recorded the temperature. Synthesis gas with a ratio of about 2 $H_2$/CO (mol/mol) was fed to the reactor such that the space velocity was about 2 standard liters of syngas/hr/gram of catalyst. The temperature during the reaction was held constant at about 225° C. The pressure was held constant at about 350 psig at the bed outlet during the reaction. Two liquid products were obtained, the heavy waxy hydrocarbon (mostly $C_{20+}$) and a mixture of water and light hydrocarbon. A standard dry gas meter measured the off-gas rate. The composition of the off-gas was measured by gas chromatography. In the attached data, the catalyst was 19% Co, 0.1% Ru on Alumina. The catalyst average particle size was 20 microns.

Figure 3:
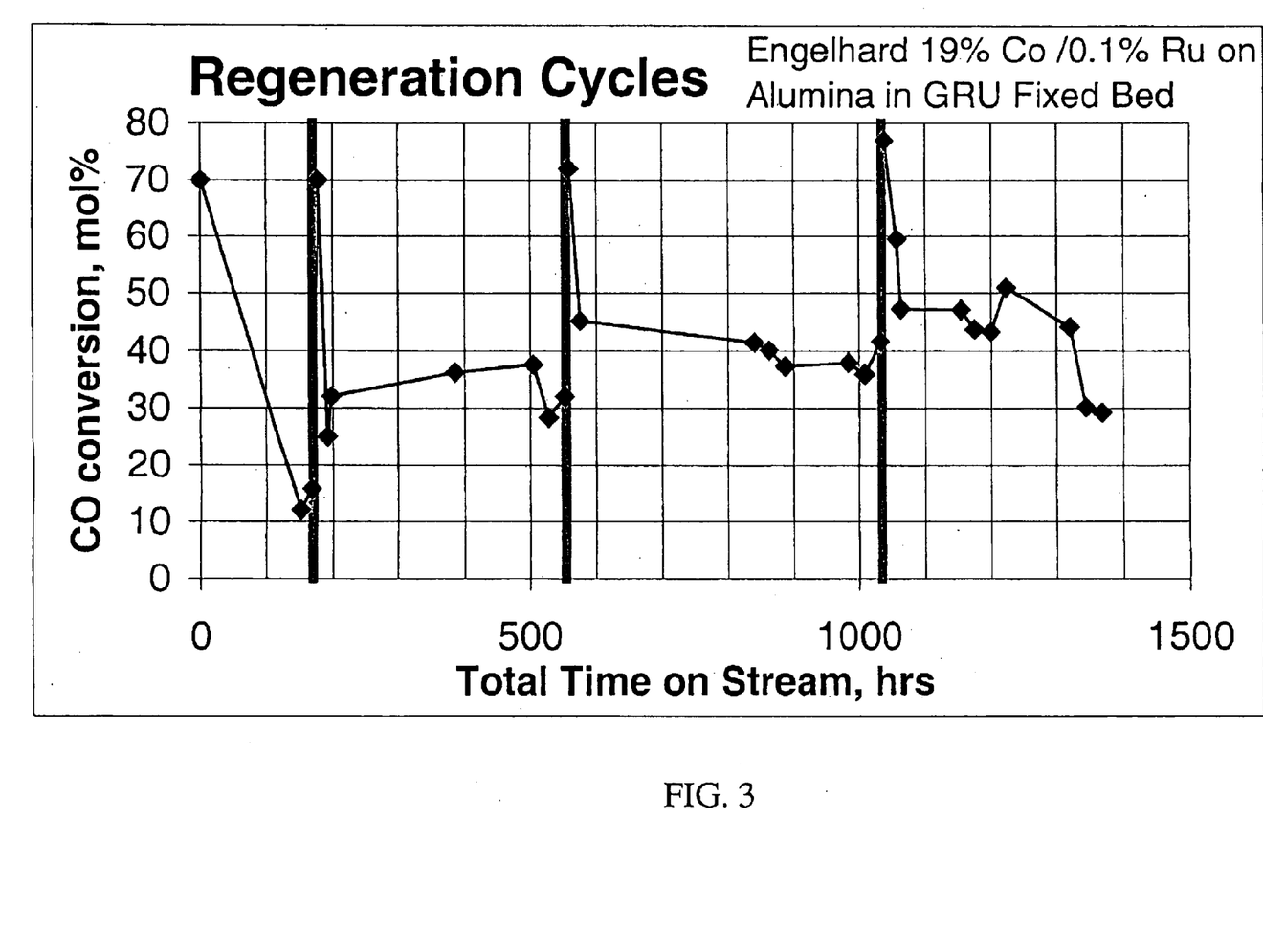
FIG. 3 is a plot of measured catalyst activity as a function of time in a process including a regeneration procedure according to an embodiment of the present invention, where the thick vertical lines indicate the beginning of the regeneration procedure.

With reference to FIG. 3, which shows the measured results, it can be seen that initially the catalyst activity produced a conversion of about 70%. The conversion fell fairly rapidly to 15% within 168 hours. At that point, the regeneration procedure was started. The feed was stopped and steam containing $H_2$ in the amount of 7% by volume was fed to the reactor. The steam was formed by vaporizing water in a line. Hydrogen gas was combined with the steam after vaporization. The W.H.S.V. was 5 grams water per gram catalyst per hour. The temperature in the reactor was maintained at about 300° C. The pressure in the reactor was maintained at about 50 psig. The regeneration gas was fed for 4 hours. At the conclusion of the regeneration procedure, the regeneration gas was stopped. The temperature was lowered back to the reaction temperature of about 225° C. Syngas feed was resumed. The catalyst activity and selectivity as measured returned to the values at pre-deactivation levels. After about an additional 300 hours, the conversion fell to 32%. The catalyst was again regenerated in the manner described above. This procedure was repeated several more times. Regeneration was effective each time in the initial activity and selectivity.

In FIG. 3 the thick vertical lines indicate the beginning of the regeneration procedure. The slight increase in activity level preceding each application of the regeneration procedure is not believed to be a general phenomenon. Causes might include slight adjustments in reaction conditions that occurred in some cases prior to regeneration. It can be seen in FIG. 3 that the conversion after regeneration was at least 70% each time the catalyst was regenerated. The data in FIG. 3 suggest that the activity falls again less than 50 hours after regeneration. However, the data in FIG. 3 also suggest that the activity is raised to a higher baseline value after each regeneration procedure. One way to keep the activity closer to its post-regeneration value for a longer period of time is to utilize a continuous regenerator. In a continuous regenerator, the catalyst is sent into a regenerator vessel that continuously applies steam. Regenerated catalyst is cycled back into the reaction zone in the Fischer-Tropsch reactor online. Thus, the average time since last regeneration of the catalyst may be minimized. In this way, the Fischer-Tropsch synthesis operates at a level closer to, for example, the high conversion peaks of the graph shown in FIG. 3

EXAMPLE 2

A fixed bed reactor was used. The fixed bed was a 1 in. tubular reactor packed with 6 grams of catalyst and about 30 grams of diluent (glass beads). A thermocouple in the middle of the bed recorded the temperature. Synthesis gas with a ratio of about 2 $H_2$/CO (mol/mol) was fed to the reactor such that the space was about 2 standard liters of syngas/hr/gram of catalyst. The temperature during the reaction was held constant at about 225° C. The pressure was held constant at about 350 psig at the bed outlet. Two liquid products were obtained, the heavy waxy hydrocarbon (mostly $C_{20+}$) and a mixture of water and light hydrocarbon. A standard dry gas meter measured the off-gas rate. The composition of the off-gas was measured by gas chromatography. In the attached data, the catalyst was 19% Co, 0.1% Ru on Alumina. The catalyst average particle size was 20 microns. Regeneration was started after the feed was on stream for a duration of between about 500 and 1000 hours. The feed was stopped and a regeneration gas was fed to the reactor. The first three rows of Table 1 summarize results for a regeneration gas including about 93% steam and about 7% hydrogen gas. The last row of Table 1 summarizes results for hydrogen gas as the regeneration gas.

In the cases of a regeneration gas including 93% steam and 7% hydrogen gas, the steam was formed by vaporizing water in a line. The W.H.S.V. was about 5 grams water per gram catalyst per hour. Hydrogen gas was combined with the steam after vaporization. In each case, the regeneration gas was fed for 4 hours. The pressure of the reaction zone was maintained at about 50 psig during regeneration. At the conclusion of the regeneration procedure, the regeneration gas was stopped. The temperature was lowered back to the reaction temperature of about 225° C. Syngas feed was resumed. The procedure was repeated, varying the hours the syngas feed was on stream in the range 500–1000 hours. The level of initial catalyst activity measured after regeneration, as the fraction of CO % conversion regained after a single regeneration is measured and displayed in Table 1.

In all the steam cases, selectivity to $C_{5+}$ and methane after regeneration was the same as the initial runs with the catalyst. However, in the case of $H_2$ gas at 350° C., the small conversion increase that occurred after regeneration came almost entirely in the form of methane. This is consistent with either sintering of the Co particles during the regeneration or preferential regeneration of methane producing sites.

Table 1 shows that there is an optimal temperature region for catalyst regeneration using a steam-containing gas. This optimal region is 200° C. and 350° C., more optimally between 250 and 350° C. and preferably close to 300° C. Referring again to Table 1, the poor performance of $H_2$ gas may have been due to sintering of the Co particles at a high temperature of 350° C. The optimal temperature for $H_2$ gas may be lower than 350° C.

TABLE 1

| Regeneration Gas | Temperature of Regeneration (° C.) | Fraction of Conversion Regained |
| --- | --- | --- |
| 93% steam/7% $H_2$ | 250 | 10 |
| 93% steam/7% $H_2$ | 300 | 95 |
| 93% steam/7% $H_2$ | 350 | 0 |
| $H_2$ gas (no steam) | 350 | 10 |

EXAMPLE 3 jA slurry reactor was used. The catalyst particle size was about 20 microns in diameter. The impeller speed was 600 rpm during reaction and regeneration. The impeller acts to suspend the catalyst particles in the solution and keeps them from settling. The catalyst was 20 wt % Co, 0.1 wt % Re on a fluorided alumina support. Suitable fluorided alumina supports are disclosed, for example, in co-pending application Ser. No. 09/314,921, commonly owned with the present application, and incorporated herein by reference. The slurry was approximately 15 wt % catalyst. The Fischer-Tropsch reaction was carried out at a pressure of about 350 psig (2.5 MPa) and a temperature of about 225° C. Table 2 shows that initially the catalyst activity produced a conversion of about 60%. The conversion fell fairly rapidly to 15% within 1014 hours. At that point, the regeneration procedure was started. The feed was stopped and steam containing about 5% $H_2$ by volume was fed to the reactor. The steam was formed by vaporizing water in a line. The W.H.S.V. was about 3 grams water per gram catalyst per hour. The temperature in the reactor was maintained at about 300° C. The pressure in the reactor was maintained at about 50 psig. The regeneration gas was fed for 4 hours. At the conclusion of the regeneration procedure, the regeneration gas was stopped. The temperature was lowered back to the reaction temperature of about 225° C. Syngas feed was resumed. The initial catalyst activity as measured was regained to 50%. The initial selectivity as measured returned to a level close to the initial level.

TABLE 2

| Time on Stream (hours) | CO Conversion (mole %) |
| --- | --- |
| 0 | 60 |
| 1014 | 15 |
| Post-regeneration | 50 |

EXAMPLE 4

A slurry reactor was used. The catalyst particle size was about 50 microns in diameter. The impeller speed was 1000 rpm during reaction and regeneration. The impeller acts to suspend the catalyst particles in the solution and keeps them from settling. The catalyst was 21 wt % Co and 0.02 wt. % Ru on a gamma alumina support. The slurry was approximately 6 wt % catalyst. The Fischer-Tropsch reaction was carried out at a pressure of about 300 psig (2.1 MPa) and a temperature of about 230° C. Table 3 shows that initially the catalyst activity produced a conversion of about 44%. The conversion fell to 27% within 325 hours. At that point, the regeneration procedure was started. The feed was stopped and nitrogen was fed to the reactor. The G.H.S.V. was about 1 Standard liters of Nitrogen per hour per gram of catalyst. The temperature in the reactor was maintained at about 240° C. The pressure in the reactor was maintained at about 50 psig. The regeneration gas was fed for 24 hours. At the conclusion of the regeneration procedure, the regeneration gas was stopped. The temperature was lowered back to the reaction temperature of about 230° C. Syngas feed was resumed. The conversion exhibited by the regenerated catalyst was 47%. The selectivity as measured returned to a level close to the initial level.

TABLE 3

| Time on Stream (hours) | CO Conversion (mole %) |
| --- | --- |
| 0 | 44% |
| 325 | 27% |
| Post-regeneration | 47% |

EXAMPLE 5

A slurry reactor was used. The catalyst particle size was about 50 microns in diameter. The impeller speed was 1000 rpm during reaction and regeneration. The impeller acts to suspend the catalyst particles in the solution and keeps them from settling. The catalyst was 21 wt % Co and 0.02 wt. % Ru on a gamma alumina support. The slurry was approximately 6 wt % catalyst. The Fischer-Tropsch reaction was carried out at a pressure of about 450 psig (3.2 MPa) and a temperature of about 210° C. Table 4 shows catalyst activity at the start of reaction, after deactivation and after regeneration in terms of relative activity. The catalyst activity at the start of reaction is designated as 100%. The catalyst relative activity fell to 33% or a third of the initial activity within 450 hours. At that point, the regeneration procedure was started. The carbon monoxide feed was stopped. The reactor was depressurized under hydrogen flow to 125 psig. The G.H.S.V. was about 1 Standard liters of hydrogen per hour per gram of catalyst. The reactor temperature was then decreased to the desired regeneration temperature. The regeneration gas was fed for 24 hours. At the conclusion of the regeneration procedure, the temperature was lowered back to the reaction temperature of about 210° C. Syngas feed was resumed.

Table 4 shows the catalyst relative activity as a function of the regeneration temperature. After a regeneration temperature of 227° C., the catalyst had regained 45% of its initial activity. After a regeneration temperature of 271° C., the catalyst had regained 71% of its initial activity.

TABLE 4

| Description | Relative Activity |
| --- | --- |
| Initial Catalyst Activity | 100% |
| Catalyst Activity at 450 hours | 33% |
| Activity after regeneration at 227° C. | 45% |
| Activity after regeneration at 271° C. | 71% |

Without further elaboration, it is believed that one skilled in the art can, using the description herein, utilize the present invention to its fullest extent. The embodiments described herein are to be construed as illustrative, and not as constraining the scope of the present invention in any way whatsoever. Furthermore, various modifications can be made without departing from the scope of the present invention. For example, while the present method has been described as a batch process, it will be understood that it can be carried out on a continuous basis, using known technologies for continuously treating catalyst.

The complete disclosures of all patents, patent documents, and publications cited herein are incorporated by reference in their entirety.

While preferred embodiments of this invention have been shown and described, modifications thereof can be made by one skilled in the art without departing from the spirit or teaching of this invention. The embodiments described herein are exemplary only and are not limiting. Many variations and modifications of the process are possible and are within the scope of the invention. Accordingly, the scope of protection is not limited to the embodiments described herein, but is only limited by the claims which follow, the scope of which shall include all equivalents of the subject matter of the claims.

What is claimed is:

1. A process for producing hydrocarbons, comprising the steps of:
    (a) carrying out a Fischer-Tropsch synthesis, comprising contacting a feed stream comprising hydrogen and carbon monoxide with a cobalt-containing catalyst in a reaction zone maintained at conversion-promoting conditions comprising a mean Fischer-Tropsch reaction pressure and a mean Fischer-Tropsch reaction temperature, said conversion-promoting conditions being effective to produce deactivated catalyst and an effluent stream comprising hydrocarbons, wherein the cobalt-containing catalyst has a pre-deactivation activity prior to the first time step (a) occurs, and wherein the activity of the catalyst drops to a deactivated level during step (a);
    (b) reducing the pressure to which at least a portion of the deactivated catalyst is subject to a regeneration pressure that is less than the mean Fischer-Tropsch reaction pressure by an amount between about 10 psig and about 300 psig;
    (c) carrying out a regeneration of said deactivated catalyst portion, comprising contacting the deactivated catalyst with a regeneration gas under regeneration-promoting conditions that include said regeneration pressure and a temperature that is between 0° C. and 150° C. higher than the mean temperature of the Fischer-Tropsch synthesis, for a period of time sufficient to reactivate the catalyst to a predetermined level of regenerated activity that equals or exceeds 50% of the pre-deactivation activity;
    (d) increasing the pressure to which the reactivated catalyst is subject to a desired Fischer-Tropsch reaction pressure after said sufficient period of time of regeneration; and
    (e) cycling through steps (a)–(d), depending on the status of the catalyst.

2. The process of claim 1 wherein the predetermined level of regenerated activity is at least 80% of the pre-deactivation activity.

3. The process of claim 1 wherein the regeneration-promoting conditions comprise a temperature between about 200° C. and about 350° C.

4. The process of claim 1 wherein the regeneration-promoting conditions comprise a temperature between about 250° C. and about 350° C.

5. The process of claim 1 wherein the volume ratio of the regeneration gas to the catalyst is at least about 0.5 standard liter per hour per gram of catalyst.

6. The process of claim 1 wherein the volume ratio of the regeneration gas to the catalyst is at least about 1 standard liter per hour per gram of catalyst.

7. The process of claim 1 wherein the regeneration gas comprises a hydrogen-containing gas.

8. The process of claim 1 wherein the regeneration gas comprises an oxygen-containing gas.

9. The process of claim 1 wherein the regeneration gas comprises steam.

10. The process of claim 1 wherein the catalyst comprises a support selected from the group consisting of silica, titania, titania/alumina, zirconia, alumina, fluorided metal oxides, borated alumina, aluminum borate, aluminum fluoride, and fluorided aluminas.

11. The process of claim 1 wherein the catalyst further comprises a promoter selected from the group consisting of ruthenium, rhenium, boron, vanadium, phosphorous, manganese, alkali metals, Sc, Ti, Zr, Hf, Rh, Pd, Os, Ir, Pt, Re, Nb, Cu, Ag and Ta.

12. The process according to claim 1 wherein step (c) is carried out in the reaction zone.

13. The process according to claim 12, wherein the reaction zone is contained in a fixed bed reactor.

14. The process according to claim 1 wherein step (b) further comprises heating said deactivated catalyst portion.

15. The process according to claim 1 wherein step (d) further comprises cooling said reactivated catalyst portion.

16. The process according to claim 1 wherein step (c) is carried out in a regeneration zone displaced from the reaction zone.

17. The process of claim 1, wherein the reaction zone is contained in a slurry bed reactor.

18. The process of claim 1 wherein the regeneration-promoting conditions comprise a pressure between about 0 psig and about 350 psig.

19. The process of claim 1 wherein the regeneration-promoting conditions comprise a pressure between about 50 psig and about 150 psig.

20. The process of claim 1 wherein the regeneration-promoting conditions comprise a pressure between about 50 psig and about 125 psig.

21. The process of claim 1, wherein the pre-deactivation activity of the catalyst comprises an initial CO conversion, and further wherein the deactivated level is equal to or less than about 62% of the initial CO conversion.

22. A process for producing hydrocarbons, comprising the steps of:

(a) carrying out a Fischer Tropsch synthesis by contacting a feed stream comprising hydrogen and carbon monoxide with a cobalt-containing catalyst in a reaction zone within a synthesis reactor to produce an effluent stream comprising deactivated catalyst and heavy hydrocarbons, the reaction zone having a mean Fischer Tropsch reaction pressure, and wherein one or more heavy hydrocarbons are deposited on said deactivated catalyst;

(b) passing at least a portion of the effluent stream from the synthesis reactor to a regeneration vessel;

(c) reducing the pressure in the regeneration vessel to a pre-determined value to effect volatilization of at least a portion of heavy hydrocarbons;

(d) contacting the cobalt-containing deactivated catalyst with a regeneration gas in the regeneration vessel under said reduced pressure, for a period of time sufficient to regenerate the catalyst;

(e) increasing the pressure in the regeneration vessel after said sufficient period of time; and (f) passing at least a portion of the regenerated catalyst back to the synthesis reactor.

* * * * *